(12) United States Patent
Pratt et al.

(10) Patent No.: US 8,449,502 B2
(45) Date of Patent: May 28, 2013

(54) SYSTEMS AND METHODS FOR POSITIONING FLUID SUPPLY SYSTEM

(75) Inventors: Benjamin Pratt, Poole (GB); Daniel Evans, Mumbles (GB); Christopher Brian Locke, Bournemouth (GB); Kenneth Mitchel Knowles, Bandera, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 13/014,482

(22) Filed: Jan. 26, 2011

(65) Prior Publication Data
US 2011/0190703 A1    Aug. 4, 2011

Related U.S. Application Data

(60) Provisional application No. 61/299,744, filed on Jan. 29, 2010.

(51) Int. Cl.
*A61M 1/00* (2006.01)

(52) U.S. Cl.
USPC ........................................... 604/151

(58) Field of Classification Search
USPC ....................... 604/82–88, 131, 151
See application file for complete search history.

(56) References Cited

U.S. PATENT DOCUMENTS

| | | | |
|---|---|---|---|
| 4,804,366 A | 2/1989 | Zdeb et al. | 604/85 |
| 4,850,978 A | 7/1989 | Dudar et al. | 604/201 |
| 5,685,842 A | 11/1997 | Drivas et al. | 604/500 |
| 6,070,761 A * | 6/2000 | Bloom et al. | 222/81 |
| 6,374,876 B2 * | 4/2002 | Bynum | 141/330 |
| 6,957,779 B2 | 10/2005 | Joshi et al. | 239/43 |

OTHER PUBLICATIONS

International Search Report and Written Opinion, issued in International Patent Application No. PCT/US2011/022571, mailed on Oct. 20, 2011.

* cited by examiner

*Primary Examiner* — Victoria P Shumate

(57) ABSTRACT

Fluid supply systems and methods for therapeutic fluid delivery systems, including those used for negative pressure wound therapy (NPWT) systems and methods.

23 Claims, 5 Drawing Sheets

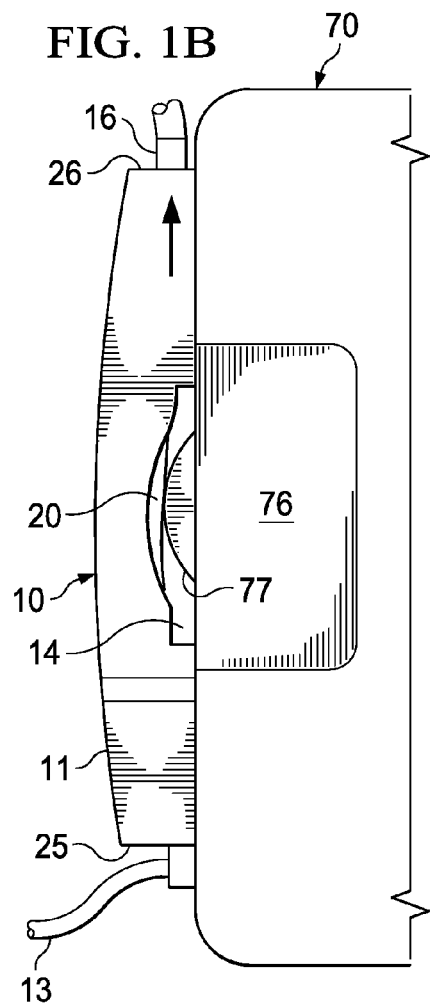
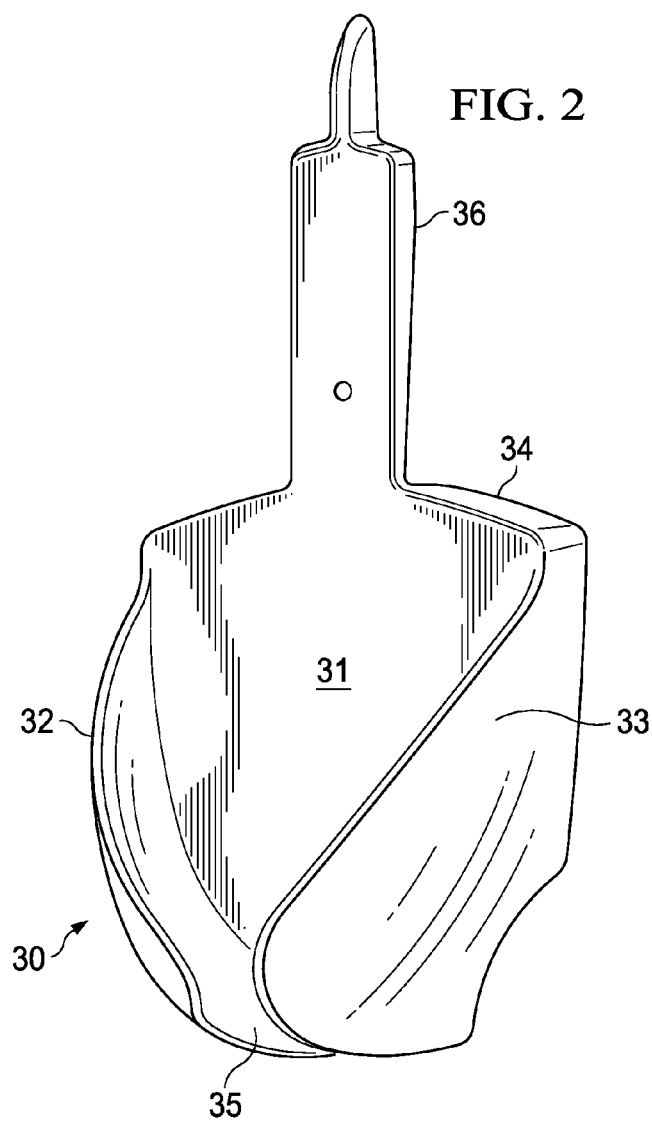

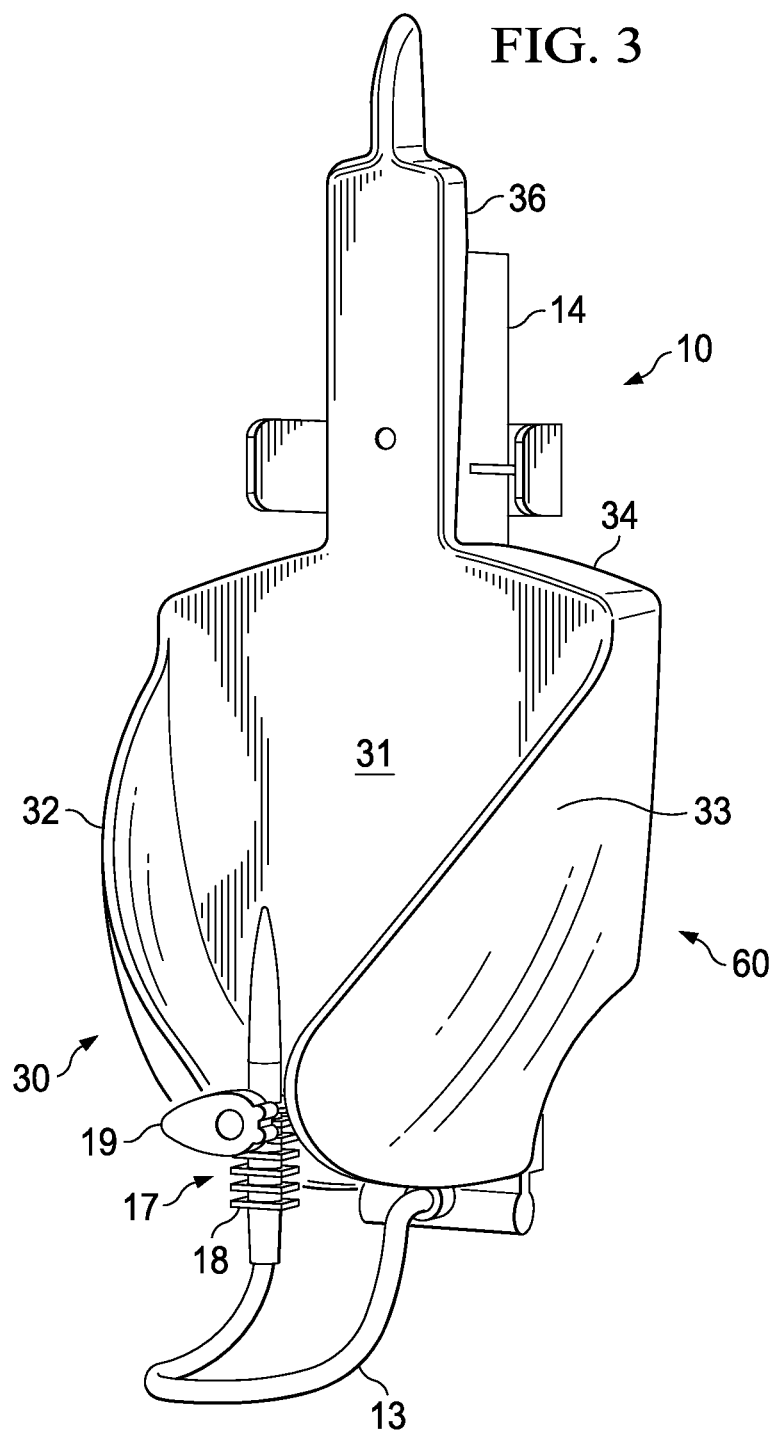

ns, or potentially a continued break in therapy.

SYSTEMS AND METHODS FOR POSITIONING FLUID SUPPLY SYSTEM

CROSS-REFERENCE TO RELATED APPLICATION

This application claims priority to U.S. Provisional Patent Application Ser. No. 61/299,744, filed Jan. 29, 2010 and entitled "Systems and Methods for Positioning Fluid Supply System" incorporated by reference herein.

BACKGROUND

1. Field of the Invention

The present invention relates generally to positioning a fluid supply system. More particularly, but not by way of limitation, the present invention relates to systems and methods for positioning a fluid supply system proximal to a therapeutic fluid delivery system used in conjunction with a negative pressure wound therapy (NPWT) system.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation of fluids (e.g., irrigation fluids and/or medicaments) may be used in conjunction with negative pressure wound therapy to promote healing and/or improve efficacy.

In addition, the delivery of therapeutic fluids (e.g. saline or antibiotic fluids) to the wound insert can also provide benefits. The connection and positioning of such fluid supply and delivery systems can challenging. In certain instances, the fluids can be located on a separate IV support, but this requires the unit to be located either on or near the support. This may present logistical issues if there is not sufficient room around the patient. If the unit is also supposed to be portable then these support methods can have a negative impact on this aspect of use.

In addition, there are various connection methods, from cartridges to basic tube routing systems that are currently used on fluid delivery pumps. Many existing systems have limiting factors on the type of fluid container that can be used with the system. For example, many cartridge systems specify a specific configuration for a fluid container or an expensive tube set for that system, leading to cost issues as well as limiting flexibility for the user in the type of fluid to be instilled.

Furthermore, securing different sized fluid containers can also present problems on portable products. Unwanted shifting of the fluid container can lead to kinks or disconnections. For NPWT systems, this can lead to leaks and blockage alarms, or potentially a continued break in therapy.

SUMMARY

The present disclosure includes embodiments of fluid supply systems and coupling such systems to therapeutic fluid delivery systems.

Certain embodiments comprise a cartridge for attachment to a fluid delivery system. In specific embodiments, the cartridge may comprise: a piercing device having a conduit, the piercing device being for piercing a liquid container and creating a fluid communication between the interior of the container and the conduit, the conduit having an outlet connection. In particular embodiments, the conduit may comprise a pump component actuated by a fluid delivery system to which the cartridge is coupled for pumping liquid from the interior of a container to the outlet connection.

In certain embodiments, the pump component may be a flexible conduit which forms a peristaltic pump upon connection to a fluid delivery system having a peristaltic pump actuator. In certain embodiments, the pump component may be a diaphragm pump configured to be actuated by an actuator of a fluid delivery system to which the cartridge is coupled.

Particular embodiments may further comprise a support device for supporting the liquid container. In certain embodiments, the piercing device may be configured to be attached to the support device such that a container placed in the support device is pierced by the piercing device. In specific embodiments, the conduit may comprise: a first coupling from the piercing device to the pump component; and a second coupling from the pump component to the outlet connection. In particular embodiments, the pump component may be a flexible conduit between the first and second couplings.

In certain embodiments, the piercing device may comprise a vent valve. Particular embodiments may comprise a fluid delivery system for connecting to a cartridge, where the fluid delivery system comprises an actuator for actuating the pump component of the cartridge. In specific embodiments, the actuator may comprise a rotor to engage the conduit of a cartridge to form a peristaltic pump. Specific embodiments may comprise a fluid delivery system, where the actuator comprises a push/pull actuator to actuate a diaphragm pump of a cartridge.

Certain embodiments comprise a fluid supply system comprising a support device configured to support a liquid container. The support device may comprise a base portion with a first lateral extension and a second lateral extension extending from the base portion, and a slot between the first lateral extension and the second lateral extension. The fluid supply system may also comprise a cartridge coupled to the support device, where the cartridge is configured to engage a fluid delivery system. In certain embodiments, the cartridge may comprise a housing comprising a first end and a second end, and a first coupling member proximal to the first end and a second coupling member proximal to the second end. Specific embodiments may comprise a piercing device coupled to a retaining member, where the retaining member is configured to engage the slot of the support device. Certain embodiments may also comprise a conduit coupled to the piercing device and the first coupling member, where the piercing device and the first coupling member are in fluid communication.

In certain embodiments, the first lateral extension and the second lateral extension may form a receptacle, and the piercing device may extend into the receptacle when the retaining member is engaged with the slot. Particular embodiments may also comprise a liquid container configured for insertion into the receptacle of the support device. In certain embodiments, the piercing device may be configured to pierce the liquid container when the liquid container is inserted into the receptacle of the support device. In specific embodiments, an upper portion of the liquid container may comprise a support engagement member.

In particular embodiments, the support engagement member may comprise an extension and an aperture. In certain embodiments, the support engagement member may be configured to engage a support member coupled to a therapeutic fluid delivery system. In particular embodiments, the first lateral extension and the second lateral extension of the support device may be curved and tapered. In specific embodiments, the fluid supply system may be coupled to a therapeutic fluid delivery system comprising a control housing having a lower support surface, and the slot may be positioned above the lower support surface. In certain embodiments, the conduit coupled to the piercing device may not be occluded when the retaining member is engaged with the slot and when the lower support surface of the control housing is placed on a flat surface.

Particular embodiments may also comprise a conduit coupled to the first and second coupling members. In certain embodiments, the conduit may be configured to engage a pump when the fluid supply system is coupled to a therapeutic fluid delivery system. In specific embodiments, the pump may be a peristaltic pump. In particular embodiments, the cartridge and the support device are integral components. In certain embodiments, the cartridge and the support device may be separate components.

Specific embodiments may also comprise a method of securing a liquid container in fluid communication with a therapeutic fluid delivery system. In particular embodiments, the method may comprise: providing a support device comprising a receptacle configured to receive the liquid container and providing a cartridge coupled to the support device, where the cartridge is configured to engage the therapeutic fluid delivery system. In certain embodiments the cartridge may comprise a piercing device, and the method may include engaging the piercing device with the support device so that the piercing device extends into the receptacle. The method may also include placing the liquid container in the receptacle of the support device, and piercing the liquid container with the piercing device.

In specific embodiments, the cartridge may comprise a housing having a first end and a second end the cartridge may comprise a first coupling member proximal to the first end and a second coupling member proximal to the second end, and the piercing device may be coupled to a conduit in fluid communication with the first coupling member. In particular embodiments, the support device may comprise a slot, the piercing device may be coupled to a retaining member, and the retaining member may be engaged with the slot of the support device when the piercing member extends into the receptacle.

In certain embodiments, the support device may comprise a base portion with a first lateral extension and a second lateral extension extending from the base portion, and the liquid container may be placed between the base portion, the first lateral extension and the second lateral extension when the liquid container is placed in the receptacle. In particular embodiments, an upper portion of the liquid container may comprise a support engagement member, and the therapeutic fluid delivery system may comprise a support member. Specific embodiments of them method may comprise engaging the support engagement member of the liquid container with the support member of the therapeutic fluid delivery system.

Certain embodiments may comprise a method of securing a liquid container in fluid communication with a therapeutic fluid delivery system.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 1B depicts a partial schematic side view of the pump-engagement cartridge coupled to a pump.

FIG. 2 depicts a perspective view of a support device for a liquid container according to an exemplary embodiment.

FIG. 3 depicts a perspective view of the pump-engagement cartridge of FIG. 1A coupled to the support device of FIG. 2.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a connection pad that "comprises," "has," "includes" or "contains" one or more elements possesses those one or more elements, but is not limited to possessing only those elements. For example, in a connection pad that comprises a fluid-delivery connection and a pressure-sensor connection, the connection pad includes the specified elements but is not limited to having only those elements. For example, such a connection pad could also include a vacuum connection.

Further, a device or structure that is configured in a certain way is configured in at least that way, but it can also be configured in other ways than those specifically described.

Figure 1A:
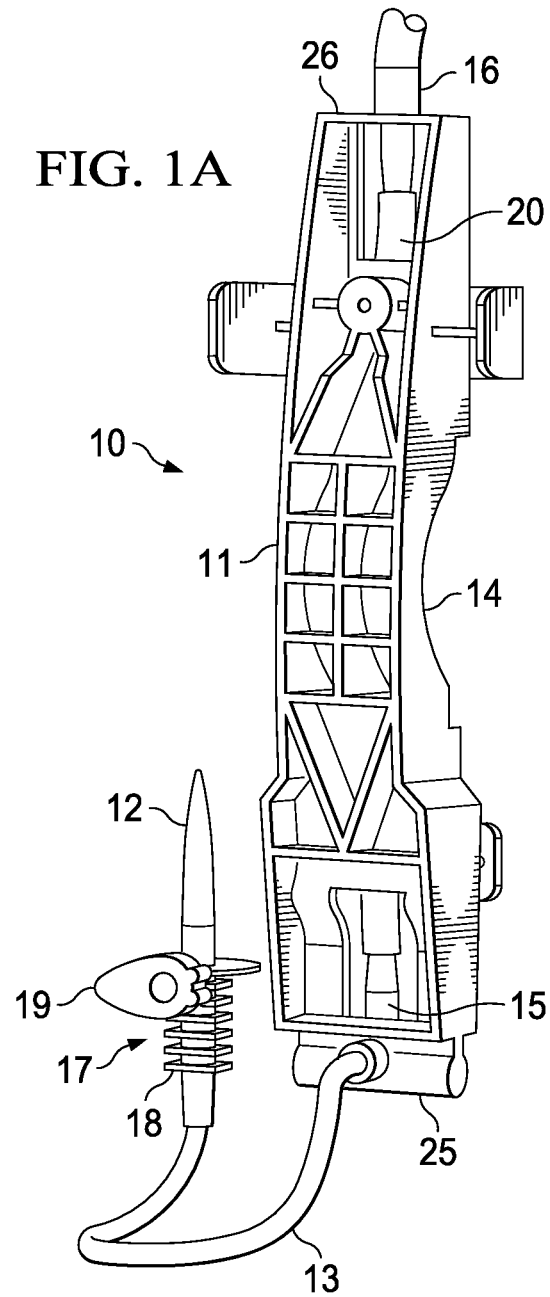
FIG. 1A depicts a perspective view of a pump-engagement cartridge according to an exemplary embodiment.

Referring now to the drawings, and more particularly to FIGS. 1A and 1B, one example of a pump-engagement cartridge 10 comprises a housing 11, a piercing device 12, and a conduit 13 coupled to piercing device 12. In the embodiment shown, housing 11 further comprise a recessed portion 14 located between a pair of conduit coupling members 15 and 16 proximal to first and second ends 25 and 26, respectively. A conduit 20 (e.g., flexible tubing) can extend between conduit coupling members 15, 16 and across recessed portion 14. As explained in more detail below, pump-engagement cartridge 10 may engage a therapeutic fluid delivery system so that the conduit between coupling members 15, 16 engages a pump (e.g., a peristaltic or diaphragm pump) to provide delivery of a therapeutic fluid.

In the partial schematic side view shown in FIG. 1B, pump engagement cartridge 10 is shown coupled to a therapeutic fluid delivery system 70 comprising a peristaltic pump 76. In this embodiment, peristaltic pump 76 comprises an actuation member or rotor 77 configured to engage conduit 20 in recess 14. In certain embodiments, conduit 20 may be located in a track or groove extending across recess 14. As rotor 77 rotates and engages conduit 20, fluid is pumped from coupling member 15 through conduit 20 and to coupling member 16. As explained in more detail below, coupling member 15 is in fluid communication with conduit 13, which can be placed in fluid communication with a fluid container. This configuration can allow peristaltic pump 76 to pump fluid from a fluid container coupled to pump engagement cartridge 10.

Figure 4:
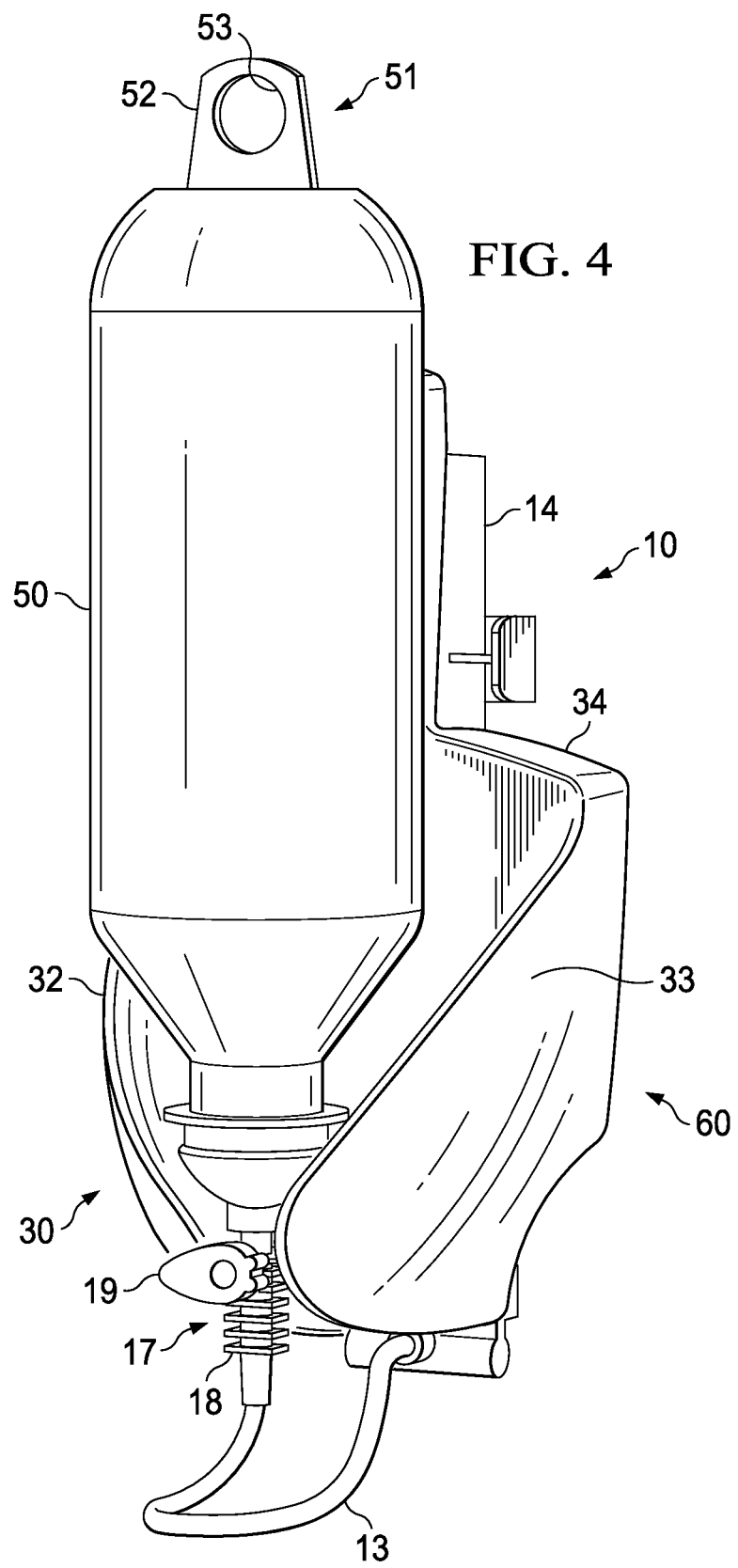
FIG. 4 depicts a fluid container coupled to the pump-engagement cartridge of FIG. 1A and the support device of FIG. 2.

Referring now to FIGS. 2-4, one example of a support device 30 configured to support a liquid container 50 is shown coupled to pump-engagement cartridge 10. FIG. 3 illustrates pump-engagement cartridge 10 and support device 30 coupled together to form a fluid supply system 60, while FIG. 4 shows liquid container 50 placed in support device 30.

As shown in FIGS. 2-4, support device 30 comprises a receptacle 31 configured to receive liquid container 50. In the embodiment shown, receptacle 31 is formed by a pair of lateral extensions 32, 33 that extend from a base portion 34. Lateral extensions 32, 33 are curved and tapered to accommodate a variety of sizes and shapes of liquid container 50. In this embodiment, lateral extensions 32, 33 are configured to provide a gap or slot 35. In the embodiment shown, support device 30 also comprises an extension 36 that extends generally vertical (when support device is positioned during use). As shown in FIGS. 3 and 4, extension 36 may be coupled to an upper portion of pump-engagement cartridge 10 and can provide additional support for liquid container 50.

As shown in the exemplary embodiment of FIG. 1A, piercing device 12 is coupled to a retaining member 17 configured to engage slot 35. In the embodiment shown, retaining member 17 comprises a plurality of flexible ribs 18 that provide a positive engagement for a friction fit between retaining member 17 and slot 35. In addition, a vent valve 19 may be coupled to piercing device 12 to allow a user to vent liquid container 50 (if needed) as it is emptied of fluid. In exemplary embodiments, piercing device 12 may comprise an elongated body with a point or taper at an end distal to retaining member 17. During use, retaining member 17 can be inserted into slot 35 so that piercing device 12 extends upward from slot 35. This arrangement provides for piercing device 12 to extend into receptacle 31 so that when liquid container 50 is inserted into receptacle 31, piercing device 12 can pierce liquid container 50. Alternatively, piercing device can be inserted into liquid container 50 prior to engaging retaining member 17 with slot 35.

Figure 5:
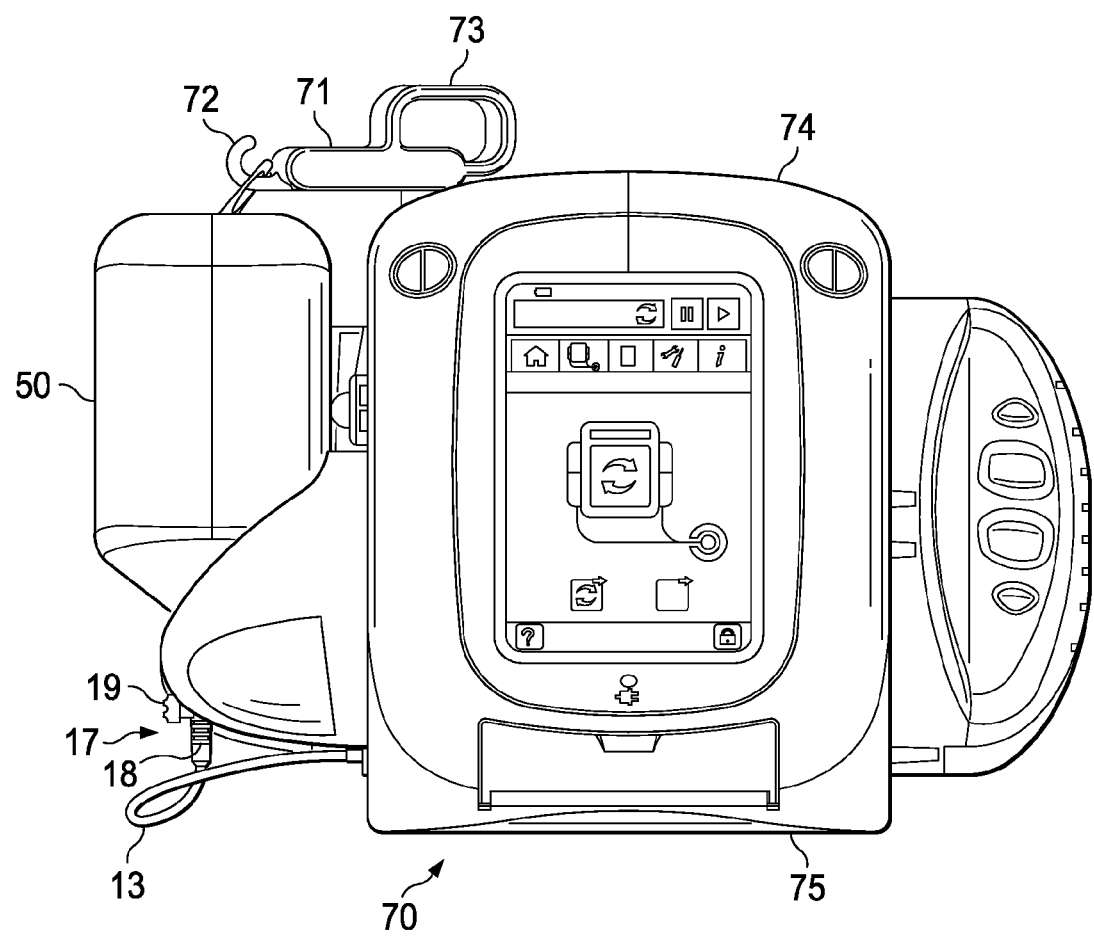
FIG. 5 depicts the assembly of FIG. 4 coupled to a therapeutic fluid delivery system.

As shown in FIG. 3, pump-engagement cartridge 10 and support device 30 can be coupled together to form a fluid supply system 60. As shown in FIGS. 4 and 5, liquid container 50 can be placed in support device 30. With this arrangement, fluid from liquid container 50 can pass through piercing device 12 (which comprises an internal conduit), conduit 13, coupling members 15, 16, and conduit 20. As shown in FIG. 5, fluid supply system 60 can be coupled to therapeutic fluid delivery system 70. In certain embodiments, therapeutic fluid delivery system 70 comprises a pump and control system configured to administer a therapeutic fluid from fluid supply system 60. In specific embodiments, therapeutic delivery system 70 may comprise a peristaltic pump that engages conduit 20 between coupling members 15, 16. In certain embodiments, therapeutic fluid delivery system 70 may be configured to deliver fluid to a negative pressure wound treatment (NPWT) system. In other embodiments, therapeutic fluid delivery system 70 may be configured to deliver fluid to other systems, including for example, those designed to administer fluids intravenously.

Fluid supply system 60 provides numerous benefits as compared to previous fluid supply systems. For example, fluid supply system 60 allows for liquid container 50 to be kept in close proximity to therapeutic fluid delivery system 70. Referring now to FIG. 4, liquid container 50 comprises a support engagement member 51 with an extension 52 and an aperture 53. As shown in FIG. 5, support engagement member 51 is configured to engage a support member 71 having a hook 72 and a handle 73. In certain embodiments, handle 73 can be extended upwardly (from the position shown in FIG. 5). Such a configuration can allow for support member 71 to support fluid containers of different lengths. Support member 71 and support device 30 can provide a stable support for the upper portion of liquid container 50.

Furthermore, support device 30 is configured to accept fluid containers of various sizes and shapes, including for example, fluid containers ranging from 250 ml to 1,000 ml. The curved and tapered shape of lateral extensions 32, 33 allow support device 30 to support a fluid container at different locations within receptacle 31. For example, a smaller fluid container may be supported at a lower position within receptacle 31 because the fluid container would enter receptacle 31 a greater distance before it engages lateral extensions 32, 33. A larger container may be supported at a higher position within receptacle 31 because it would engage lateral extensions 32, 33 sooner than a smaller fluid container. The engagement of piercing device 12 with a fluid container, along with the engagement of retaining member 17 with slot 35 can stabilize the lower portion of a fluid container inserted into receptacle 31. In addition, the engagement of support member 71 and support engagement member 51 provides stability to the upper portion of the fluid container. These features allow a user to utilize different types of fluid containers and does not require fluid containers specifically designed for this fluid supply system. Such specialized containers can often increase the costs associated with fluid supply systems.

In addition, fluid supply system and therapeutic fluid delivery system 70 are configured so that the systems may be supported by a flat surface without kinking or pinching conduit 13. As shown in FIG. 5, therapeutic fluid delivery system 70 comprises a control unit housing 74 having a lower surface 75 that can be used to support therapeutic fluid delivery system 70 when placed on a flat surface. In this embodiment, retaining member 17 (which is coupled to conduit 13) is located above lower surface 75 of control unit housing 74. This configuration allows therapeutic fluid delivery system 70 to be supported on a flat surface without causing conduit 13 to become occluded (e.g., pinched or kinked) under components such as control unit housing 74 or retaining member 17.

The various illustrative embodiments of devices, systems, and methods described herein are not intended to be limited to the particular forms disclosed. Rather, they include all modifications and alternatives falling within the scope of the claims. For example, the support device may be integrated with a side cover coupled to the therapeutic fluid delivery system. Such an a configuration can assist in accommodating larger bottles. The side cover can also be used to protect the delivery mechanism when not in use or during storage. In addition, certain embodiments may utilize spring-loaded straps around the fluid container to assist in securing the fluid container within the receptacle of the support device. Furthermore, certain embodiments may not comprise a support device with a receptacle, but instead utilize the piercing device in conjunction with straps and/or a side cover. In certain embodiments, the support device and cartridge are integral components, while in other embodiments, they may be separate components. In still other embodiments, the fluid container may be integral to the support device or pump engagement cartridge, and the system may not include a piercing device. For example, a fluid container may be integrally formed with pump engagement cartridge 10 and comprise a port that can be coupled to conduit 13. Such a configuration could reduce the need to include a piercing device to assist in stabilization of the fluid container, due to the fluid container being integrally formed with the pump engagement cartridge.

Certain embodiments may comprise a load cell to prevent the fluid container from running empty and to provide an indicator of fluid level.

The claims are not intended to include, and should not be interpreted to include, means-plus- or step-plus-function limitations, unless such a limitation is explicitly recited in a given claim using the phrase(s) "means for" or "step for," respectively. It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of this invention.

The invention claimed is:

1. A cartridge adapted to be attached to a fluid delivery system, the cartridge comprising:
    a piercing device having a conduit, the piercing device adapted to pierce a liquid container to provide fluid communication between the liquid container and the conduit, the conduit having an outlet connection,
    wherein the conduit comprises a pump component, the pump component comprising a flexible tube adapted to be positioned between an actuator and the cartridge, the actuator carried by the fluid delivery system, wherein the pump component is adapted to engage the actuator to pump liquid from the container to the outlet connection.

2. The cartridge according to claim 1, wherein the pump component is adapted to provide a peristaltic pump upon attachment of the cartridge to the fluid delivery system, the actuator carried by the fluid delivery system being a peristaltic pump actuator.

3. The cartridge according to claim 1, further comprising a support device for supporting the liquid container.

4. The cartridge according to claim 3, wherein the piercing device is configured to be attached to the support device such that a container placed in the support device is pierced by the piercing device.

5. The cartridge according to claim 1, the conduit further comprising:
    a first coupling from the piercing device to the pump component; and
    a second coupling from the pump component to the outlet connection.

6. The cartridge according to claim 5, wherein the flexible tube between the first and second couplings.

7. The cartridge according to claim 1 wherein the piercing device comprises a vent valve.

8. A fluid delivery system for connecting to a cartridge according to claim 1, the fluid delivery system comprising an actuator for actuating the pump component of the cartridge.

9. The fluid delivery system according to claim 8, wherein the actuator comprises a rotor adapted to engage the flexible tube to form a peristaltic pump.

10. The fluid delivery system according to claim 8, wherein the actuator comprises a push/pull actuator adapted to actuate a diaphragm pump of a cartridge.

11. A fluid supply system comprising:
    a support device configured to support a liquid container, wherein the support device comprises:
        a base portion with a first lateral extension and a second lateral extension extending from the base portion; and
        a slot between the first lateral extension and the second lateral extension; and
    a cartridge coupled to the support device, wherein the cartridge is configured to engage a fluid delivery system and wherein the cartridge comprises:
        a housing comprising a first end and a second end;
        a first coupling member proximal to the first end and a second coupling member proximal to the second end;
        a flexible conduit positioned in fluid communication between the first coupling member and the second coupling member, the flexible conduit adapted to be engaged by an actuator carried by the fluid delivery system and to be positioned between the actuator and the housing;
        a piercing device coupled to a retaining member, wherein the retaining member is configured to engage the slot of the support device; and
        a conduit coupled to the piercing device and the first coupling member, wherein the piercing device and the first coupling member are in fluid communication.

12. The fluid supply system of claim 11 wherein the first lateral extension and the second lateral extension form a receptacle, and wherein the piercing device extends into the receptacle when the retaining member is engaged with the slot.

13. The fluid supply system of claim 12 further comprising a liquid container configured for insertion into the receptacle of the support device.

14. The fluid supply system of claim 13 wherein the piercing device is configured to pierce the liquid container when the liquid container is inserted into the receptacle of the support device.

15. The fluid supply system of claim 13 wherein an upper portion of the liquid container comprises a support engagement member.

16. The fluid supply system of claim 15 wherein the support engagement member comprises an extension and an aperture.

17. The fluid supply system of claim 15 wherein the support engagement member is configured to engage a support member coupled to a therapeutic fluid delivery system.

18. The fluid supply system of claim 11 wherein the first lateral extension and the second lateral extension of the support device are curved and tapered.

19. The fluid supply system of claim 11 wherein: the fluid supply system is coupled to a therapeutic fluid delivery system comprising a control housing having a lower support surface; and wherein the slot is positioned above the lower support surface.

20. The fluid supply system of claim 19 wherein the conduit coupled to the piercing device is not occluded when the retaining member is engaged with the slot and when the lower support surface of the control housing is placed on a flat surface.

21. The fluid supply system of claim 11, wherein the flexible conduit is adapted to provide a peristaltic pump when engaged by the actuator.

22. The fluid supply system of claim 11 wherein the cartridge and the support device are integral components.

23. The fluid supply system of claim 11 wherein the cartridge and the support device are separate components.

* * * * *